United States Patent [19]

Gutwein et al.

[11] Patent Number: 4,473,447
[45] Date of Patent: Sep. 25, 1984

[54] METHOD OF MANUFACTURING ABSORPTION LAYERS FOR SOLAR ENERGY SYSTEMS AND BATH THEREFOR

[75] Inventors: Herbert Gutwein, Pasenbach; Edwin Erben, Munich; August Mühlratzer, Gilching; Boy Cornils, Dinslaken; Bela Tihanyi, Schermbeck; Werner DeWin, Dinslaken, all of Fed. Rep. of Germany

[73] Assignee: MAN Maschinenfabrik Augsburg-Nurnberg AG, Munich, Fed. Rep. of Germany

[21] Appl. No.: 405,217

[22] Filed: Aug. 4, 1982

[30] Foreign Application Priority Data

Aug. 10, 1981 [DE] Fed. Rep. of Germany ....... 3131576
Apr. 8, 1982 [DE] Fed. Rep. of Germany ....... 3213270

[51] Int. Cl.$^3$ ............................ C25D 3/12; C25D 3/56
[52] U.S. Cl. ................................... 204/43 T; 204/48; 204/49
[58] Field of Search ................. 204/48, 49, 45 R, 43 T

[56] References Cited

U.S. PATENT DOCUMENTS

| | | | |
|---|---|---|---|
| 3,031,386 | 4/1962 | Tsu et al. | 204/43 T |
| 3,032,485 | 5/1962 | Tsu et al. | 204/43 T |
| 3,032,486 | 5/1962 | Sallo et al. | 204/43 T |
| 3,041,254 | 6/1962 | Pedler | 204/49 |
| 3,239,437 | 3/1966 | Stephen | 204/48 X |
| 3,380,151 | 4/1968 | Parsons | 204/48 X |
| 3,417,005 | 12/1968 | Baig | 204/49 X |
| 3,488,264 | 1/1970 | Bailey et al. | 204/49 |
| 3,496,074 | 2/1970 | Welling | 204/48 X |
| 3,543,390 | 12/1970 | Parsons | 204/48 X |
| 3,547,787 | 12/1970 | Parsons | 204/48 X |
| 3,556,959 | 1/1971 | Passal | 204/49 |

OTHER PUBLICATIONS

W. A. Wesley et al., "Electrodeposition of Nickel at High Current Density", Reprint 36th Annual Proc. Am. Eletroplaters Soc., pp. 1–16, (1949).

Primary Examiner—G. L. Kaplan
Attorney, Agent, or Firm—Alan H. Levine

[57] ABSTRACT

Method for manufacturing solar absorption layers by electrodeposition of heavy metals, such as Ni and Co, from aqueous citrate solutions. The heavy metal citrates are produced by direct reaction of metal oxides or carbonates with citric acid. The electrolyte concentration is a maximum 5% and has a pH of between 8 and 11. The deposition process takes place at room temperature, bath voltages of 8 to 30 V, and current densities of 3 to 10 A/dm$^2$. The layers produced by this method are well bonded black layers resistant to temperatures up to 700° C.

9 Claims, No Drawings

METHOD OF MANUFACTURING ABSORPTION LAYERS FOR SOLAR ENERGY SYSTEMS AND BATH THEREFOR

This invention relates to a method of manufacturing absorption layers for solar energy systems by electrodeposition.

Absorption layers play an important part in the photothermic conversion of energy. The state of the art comprises various absorption layers, e.g., the time-tested black chromium layers. These layers, however, are designed for low-temperature ranges, i.e., only to 300° C. maximum.

In a broad aspect of the present invention, the method of this general description enables suitable absorption layers to be manufactured having high resistance to temperature.

It is a particular object of the present invention to manufacture the absorption layer by the electrodeposition of heavy metals from aqueous citrate solutions. This enables sufficiently absorbant absorption layers to be manufactured that will resist temperatures as high as 700° C.

The heavy metal citrates are preferably obtained by direct reaction of metal hydroxides or carbonates with citric acid. The heavy metal citrate solutions obtained in this manner can as such be readily isolated in pure form by way of crystallization or spray drying. The heavy metal used is Ni or preferably Co., or other metals of a specific weight greater than 4 gms/cm$^3$.

In a further aspect of the present invention, heavy metal citrate is obtained by dissolving citric acid in water at about 80° C. and causing it to react, at a temperature of about 100° C., with a mash of cobalt (II) hydroxide carbonate or nickel (II) hydroxide carbonate, the water being added slowly. The concentrations preferably are citric acid/water=3.66 mol/liter and cobalt (II) or nickel (II) hydroxide carbonate/water=1 mol/liter. After filtration and spray drying, the resultant cobalt hydrate or nickel hydrate will contain nearly 100% of the cobalt or nickel feed.

In a further aspect of the present invention, the citric acid is dissolved in water at about 80° C. and partially reacted at a temperature of about 100° C., with cobalt (II) hydroxide carbonate being slowly added, and after a reaction time of about 20 minutes, it is fully reacted with nickel (II) hydroxide carbonate being added. The metal citrate is preferably then obtained from the solution by fractional crystallization.

For electrodeposition, use is made of a diluted, aqueous heavy metal citrate solution of less than 5% by weight, preferably 1% by weight, the pH value of which runs between 8 and 11, deposition being achieved while the bath is strongly agitated. Using 5 to 10 grams/liter (g/l) NH$_4$Cl as a supporting electrolyte, the current density can be raised for the deposition process. It has been shown that this will still improve the resistance of the absorption layer to temperature. The intended pH value of the heavy metal solution is standardized with ammonia. In this manner advantageous black absorption layers can be obtained.

Especially well-adhering absorption layers can be produced at bath voltages of 15 to 25 V and current densities of 1 to 5 A/dm$^2$, and at room temperature. Using the supporting electrolyte, the current density can be raised as high as 10 A/dm$^2$ at a voltage of 8 to 30 V.

For example, heavy metal citrates were produced according to the invention as follows:

EXAMPLE 1

422.4 g citric acid were dissolved in 600 ml water, heated to about 80° C., and reacted at a temperature of 100° C. with a mash of 315.2 g cobalt (II) hydroxide carbonate in 1400 ml water, which was added slowly. After filtration and spray drying, 704.4 g cobalt citrate of a cobalt content of 24.8% by weight was obtained, which is about equivalent to 99% by weight of the cobalt feed.

From the heavy metal citrate produced in this manner, a diluted aqueous solution of 1% by weight in an ammonical medium was made. With the ammonia, the pH value of this electrolyte solution was standardized to about 9. The deposition was made at a bath voltage of 15 to 25 V, a current density of 1 to 5 A/dm$^2$ and at room temperature.

The layers produced in this manner are characterized by high absorption in the visible spectral range and by high resistance to temperature.

EXAMPLE 2

211.2 g citric acid were dissolved in 900 ml water at about 80° C. and partially reacted at a temperature of 100° C. with 78.8 g cobalt (II) hydroxide carbonate being added slowly. After a reaction time of 20 minutes, 96.7 g nickel (II) hydroxide carbonate were added for reaction. Upon dissolution, the solution mixture was subjected to fractional crystallization. The 185.8 g crystals obtained in the main fraction at about 20° C. contained 14.7% by weight cobalt and 16.7% by weight nickel.

From this heavy metal citrate, a diluted aqueous electrolyte solution was made with the addition of 1% by weight ammonia and about 7 g/l ammonium chloride (NH$_4$Cl). Deposition was achieved at room temperature, a bath voltage of 8 to 30 V, and a current density of 3 to 10 A/dm$^2$.

The absorption layer produced in this manner possesses even better resistance to temperature than the layer produced in Example 1.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

What is claimed is:

1. A method of making radiation-absorbing black metal coatings by electrodeposition of metal from an aqueous electrolyte solution, comprising the steps of:
   directly reacting citric acid with a metal hydroxide and/or carbonate selected from the group consisting of nickel hydroxide, nickel carbonate, cobalt hydroxide, and cobalt carbonate to produce nickel citrate and/or cobalt citrate,
   preparing an aqueous solution of the nickel and/or cobalt citrate, adjusting the pH of the solution with ammonia to between 8 and 11, the solution containing no more than 5% by weight of the metal citrate, and containing substantially no other citric acid salts other than a slight amount of ammonium citrate resulting from adjustments of the pH with ammonia and electrodepositing black nickel or cobalt from the solution at room temperature.

2. A method as defined in claim 1 wherein the citrate is prepared by dissolving citric acid in water at a temperature of about 80° C., and subsequently adding a mash of cobalt (II) hydroxycarbonate in water at a temperature of about 100° C.

3. A method as defined in claim 2 wherein in the citric acid solution the citric acid is used in a concentration of 3 to 4 moles/L, and in the mash the cobalt (II) hydroxycarbonate is used in a concentration of about 1 mole/L.

4. A method as defined in claim 2 wherein after about 20 minutes of reaction time, a mash of nickel (II) hydroxycarbonate in water is added to the citric acid and cobalt (II) hydroxycarbonate mixture.

5. A method as defined in claim 2 wherein in the citric acid solution the citric acid is used in a concentration of between 1 and 1.5 moles/L of water, in the cobalt II mash cobalt (II) hydroxycarbonate is used in a concentration of between 0.3 and 0.4 moles/L of water, and in the nickel (II) mash nickel (II) hydroxycarbonate is used in a concentration of between 0.4 and 0.5 moles/L of water.

6. A method as defined in claim 1 wherein the aqueous solution contains about 1% citrate.

7. A method as defined in claim 1 wherein the aqueous solution contains 5 to 10 g/L of ammonium chloride as a conducting salt.

8. A method as defined in claim 1 wherein the electrodeposition is carried out using a voltage of 8 to 30 volts, and a cathode current density of 1 to 10 amp/dm$^2$.

9. An aqueous electroplating bath for depositing radiation-absorbing black metal coatings comprising the reaction product of citric acid with a metal hydroxide and/or carbonate selected from the group consisting of nickel hydroxide, nickel carbonate, cobalt hydroxide and cobalt carbonate in an aqueous solution, the pH of the bath being adjusted with ammonia to between 8 and 11, the bath containing no more than 5% by weight of the metal citrate and containing substantially no other citric acid salts other than a slight amount of ammonium citrate resulting from adjustment of the pH with ammonia.

* * * * *